(12) United States Patent
IJpeij et al.

(10) Patent No.: US 7,816,548 B2
(45) Date of Patent: Oct. 19, 2010

(54) METHOD OF PREPARING A HYDROCARBYLATED METAL-ORGANIC COMPOUND

(75) Inventors: Edwin IJpeij, Sittard (NL); Felix Beijer, Sittard (NL); Henricus Arts, Munstergeleen (NL); Gerardus Van Doremaele, Sittard (NL)

(73) Assignee: DSM IP Assets B.V., TE Heerlen (NL)

( * ) Notice: Subject to any disclaimer, the term of this patent is extended or adjusted under 35 U.S.C. 154(b) by 1141 days.

(21) Appl. No.: 10/566,978

(22) PCT Filed: Aug. 3, 2004

(86) PCT No.: PCT/EP2004/008712

§ 371 (c)(1),
(2), (4) Date: Jul. 3, 2006

(87) PCT Pub. No.: WO2005/014669

PCT Pub. Date: Feb. 17, 2005

(65) Prior Publication Data

US 2007/0112182 A1     May 17, 2007

Related U.S. Application Data

(60) Provisional application No. 60/537,916, filed on Jan. 22, 2004.

(30) Foreign Application Priority Data

Aug. 4, 2003   (EP) .................................. 03077434
Nov. 25, 2003  (EP) .................................. 03078723

(51) Int. Cl.
C07F 5/00    (2006.01)
C07F 15/00   (2006.01)
(52) U.S. Cl. ............................ 556/9; 556/19; 548/101; 534/15
(58) Field of Classification Search .................. 556/7, 556/19, 9; 534/15; 548/101
See application file for complete search history.

(56) References Cited

FOREIGN PATENT DOCUMENTS

| CA | 2243726      | 1/2000 |
| WO | WO 96/13529  | 5/1996 |
| WO | WO 02/070569 | 9/2002 |

OTHER PUBLICATIONS

Zhang et al., J. Am. Chem. Soc., vol. 122, No. 23, pp. 5499-5509 (2000).*

Stephan et al., Organometallics, vol. 18, No. 7, pp. 1116-1118 (1999).*
International Search Report, (2004).
Ulrich Siemeling et al; "Synthesis and Structure of [Nbcl$_3${[NPPh$_2$(C$_5$H$_4$)]$_2$Fe}]: The First Structurally Characterised Complex Containing a chelating Di(phosphaneiminato) Ligand"; Z. Anorg. Allg. Chem. 2000 ; vol. 626, No. 4, pp. 825-826.
Matthew G. Thorn et al; "Synthesis and Chemistry of Titanacyclopentane and Titanacyclopropane Rings Supported by Aryloxie Ligation"; 1997 American Chemical Society; vol. 119, pp. 8630-8641.
John E. Hill et al; "Formation, Fragmentation, and Isomerization of Azatitanacycle Rings Supported by Aryloxide Ligation"; Organometallics 1992; vol. 11, pp. 1775-1777; 1992 American Chemical Soceity.
Kattesh V. Katti et al; "Synthesis and Characterization of New Heterocyclic Compounds of Tungsten, Selenium, and Tellurium"; Inorg. Chem. 1987; vol. 26, pp. 814-816.
Herbert W. Roesky et al; "Wolframheterocyclen mit Phosphor, Schwefel und Stickstoff als Ringbausteine"; Chem. Ber. vol. 122, No. 1, (1989); pp. 63-65.
Herbert W. Roesky et al; "Darstellung eines cyclischen Ferrocenderivates mit Wolfram(VI)"; Organische Chemie; vol. 43, No. 2, 1988, pp. 231-232.

* cited by examiner

*Primary Examiner*—Porfirio Nazario Gonzalez
(74) *Attorney, Agent, or Firm*—Nixon & Vanderhye P.C.

(57) ABSTRACT

The invention relates to a process for the preparation of a hydrocarbylated metal organic compound, comprising a hydrocarbyl group, a spectator ligand and optionally a ligand, by contacting a metal-organic reagent with a spectator ligand in the presence of at least 2 equivalents of a hydrocarbylating agent. The invention further relates to a hydrocarbylated metal organic compound according to the following formula

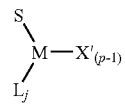

containing a spectator ligand S equal to $(Ar-Z-)_s Y(-Z-DR'_n)_q$, wherein Y represents the an anionic moiety of S bonded to M of the metal-organic compound, Z an optional bridging group between the Y moiety and the $DR'_n$ and/or Ar group, D an electron donating hetero atom chosen from group 15 or 16, R' an optional substituent, Ar an electron-donating aryl group, n the number of R' groups bonded to D, q and s integers with $q+s \geq 1$, wherein Y is an imine radical, or wherein the electron donating hetero atom containing group $DR'_{-n}$ is a ketimide, phosphinimide, guanidine, or iminoimidazoline, or a combination thereof.

12 Claims, No Drawings

METHOD OF PREPARING A HYDROCARBYLATED METAL-ORGANIC COMPOUND

This application is the US national phase of international application PCT/EP2004/008712 filed 3 Aug. 2004 which designated the U.S. and claims benefit of EP 03077434.3, dated 4 Aug. 2003, EP 03078723.8, dated 25 Nov. 2003 and U.S. 60/537,916, dated 22 Jan. 2004, the entire content of which is hereby incorporated by reference.

The invention relates to an improved process for preparing a hydrocarbylated metal organic-compound comprising a hydrocarbyl group, a spectator ligand and optionally a neutral ligand. In this application under a hydrocarbyl group, in addition to its normal meaning, is also understood a hydride group.

Processes for the preparation of hydrocarbylated metal organic compounds are known in the art. In general these compounds are prepared by at least a three step process: (i) reaction of a spectator ligand with a strong base giving a spectator ligand salt, followed by either (iia) contacting this ligand salt with a metal-organic reagent, or (iib) contacting this ligand salt with trimethylsilylchloride (TMSCl), giving the TMS-substituted ligand which is, after purification, further contacted with a metal-organic reagent forming a reaction product followed by (iii) contacting this reaction product with a hydrocarbylating agent. Disadvantage of the known methods is thus that they all use more than one reaction step to prepare the hydrocarbylated metal organic compound.

Purpose of the invention is to provide a method for the preparation of a hydrocarbylated metal-organic compound from a metal-organic reagent in one step only.

This purpose is achieved by contacting a metal-organic reagent with a spectator ligand in the presence of at least 2 equivalents, with respect to the metal-organic reagent, of a hydocarbylating agent.

With the process of the invention a hydrocarbylated metal organic compound can be made in a one step process, whereby the metal-organic compound comprises at least one spectator ligand more than the metallic organo reagent.

In the process of the invention hydrocarbylating agents are nucleophilic groups comprising a metal-, or metalloid carbon or hydride bond.

Examples of hydrocarbylating agents are: tri-, or tetrahydrocarbyl boron, tri-, or tetrahydrocarbyl aluminium, tri-, or tetrahydrocarbyl gallium, tri-, or tetrahydrocarbyl indium and di-, or tetrahydrocarbyl tin.

Preferably the hydrocarbylating agent comprises a metal or a metalloid chosen from group 1, 2, 11, 12, 13 or 14. Examples of hydrides from metals or metalloids of group 1, 2, 11, 12, 13, 14 include: lithiumhydride, sodiumhydride, potassiumhydride, calciumhydride, magnesiumhydride, copperhydride, zinchydride, cadmiumhydride, borane, aluminumhydride, galliumhydride, siliconhydride, germaniumhydride, and tinhydride.

Preferably the hydrocarbylating agent comprises Li, Mg, Zn, or Al.

Examples of Li comprising hydrocarbylating agents are methyllithium, phenyllithium, benzyllithium, biphenyllithium, naphtyllithium, lithio-dimethylresorcinol, and lithio-N,N-dimethylaniline.

Examples of magnesium comprising hydrocarbylating agents are methylmagnesiumhalide, phenylmagnesiumhalide, benzylmagnesiumhalide, biphenylmagnesiumhalide, naphtylmagnesiumhalide, tolylmagnesiumhalide, xylylmagnesiumhalide, mesitylmagnesiumhalide, dimethylresorcinolmagnesiumhalide, N,N-dimethylanilinemagnesiumhalide, dimethylmagnesium, diphenylmagnesium, dibenzylmagnesium, (biphenylene)magnesium, dinaphtylmagnesium, ditolylmagnesium, dixylylmagnesium, dimesitylmagnesium, bis(dimethylresorcinol)magnesium, and bis(N,N-dimethylaniline)magnesium.

Examples of aluminium comprising hydrocarbylating agents are diisobutylaluminium hydride, $C_1$-$C_{20}$ trihydrocarbyl aluminium, and hydrocarbylaluminoxanes.

In the process of the invention the metal-organic reagent can be represented by formula 1:

$$ML_jX_p \qquad \text{(formula 1)}$$

wherein M is a metal from group 3-11, X a monoanionic ligand bonded to M, L a neutral Lewis based ligand bonded to M, j an integer denoting the number of neutral ligands L and p is the valency of the metal M.

Each anionic ligand, X, may be independently selected from the group consisting of monoanionic spectator ligands, hydride, halide, alkyl, silyl, germyl, aryl, amide, aryloxy, alkoxy, phosphide, sulfide, acyl, pseudo halides such as cyanide, azide, acetylacetonate, etc., or a combination thereof. Preferably, X is hydride or a moiety selected from the group consisting of monoanionic spectator ligands, halide, alkyl, aryl, silyl, germyl, aryloxy, alkoxy, amide, siloxy and combinations thereof (e.g. alkaryl, aralkyl, silyl substituted alkyl, silyl substituted aryl, aryloxyalkyl, aryloxyaryl, alkoxyalkyl, alkoxyaryl, amidoalkyl, amidoaryl, siloxyalkyl, siloxyaryl, amidosiloxyalkyl, haloalkyl, haloaryl, etc.) having up to 20 non-hydrogen atoms.

Examples of Lewis basic ligands (L) include ethers, such as tetrahydrofuran (THF), diethylether, thioethers, like thiophene, diethylsulfide, dimethylsulfide, amines, such as trialkylamines, pyridine, bipyridine, TMEDA, (−)-sparteine), phosphanes and diphosphanes, such as triphenylphoshine, trialkylphosphanes, bidentate alkyl or aryldiphoshanes). The amount of ligands (X and L) depends on the valency of the metal and the stability of the metal-organic reagent. The metal-organic reagent may be monomeric, oligomeric or a cluster. The number of anionic ligands equals the valency of the metal used. The number of neutral ligands on the metal-organic reagent may range from 0 to the amount that satisfies the 18-electron rule, as known in the art.

In the method of the invention a spectator ligand can be a monoacidic spectator ligand, a diacidic spectator ligand, a monoacidic bidentate spectator ligand, or a Lewis basic bi-, or multidentate spectator ligand.

An example of a mono acidic spectator ligand is an imine ligand according to formula 2, or the HA adduct thereof, wherein HA represents an acid, of which H represents its proton and A its conjugate base,

$$Y=N-R \qquad \text{(formula 2)},$$

wherein Y is selected from a substituted carbon, nitrogen or phosphorous atom and R represents a substituent. If Y represents a substituted carbon atom, the number of substituents is 2. If Y represents a substituted nitrogen atom, the number of substituents is 1 and the number of substituents is 1 or 3 if Y represents a phosphorous atom, depending on the valency of the phosphorous atom.

Substituents on carbon, nitrogen or phosphorous may be equal or different, optionally linked with each other, optionally having hetero atoms. Substituents may be protic or aprotic.

A protic substituent is defined here as a substituent which has at least one group 15 or group 16 atom containing at least one proton.

Examples of protic substituents include $C_1$-$C_{20}$ linear, branched or cyclic hydrocarbyl radicals, substituted with a group 15 or 16 atom bearing at least one hydrogen atom. Preferred protic substituents include phenolic radicals, pyrrolic radicals, indolic radicals, and imidazolic radicals.

The substituent is called aprotic if the substituent lacks a group containing a group 15 or group 16 atom bearing a proton. An unsubstituted aprotic hydrocarbyl radical can be a $C_1$-$C_{20}$ linear, branched or cyclic radical, a hydrogen atom, a halogen atom, a group 14 oxy radical—such as a $C_{1-8}$ alkoxy radical, a $C_{6-10}$ aryl or aryloxy radical, silyloxy radical, germanyloxy radical, stannyloxy radical—an amido radical, or a $C_{1-20}$ hydrocarbyl radical unsubstituted or substituted by a halogen atom, a $C_{1-8}$ alkoxy radical, a $C_{6-10}$ aryl or aryloxy radical, an amido radical, a silyl radical of the formula:

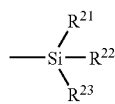

(formula 3)

or a germanyl radical of the formula:

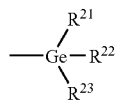

(formula 4)

wherein $R^{2j}$ with j=1 to 3 is independently selected from the group consisting of hydrogen, a $C_{1-8}$ alkyl or alkoxy radical, $C_{6-10}$ aryl, aryloxy radicals a silyl redical of formula 3 or a germanyl radical of formula 4, each substituent $R^{2j}$ may be linked with another $R_{2j}$ to form a ring system.

The substituent R can be H, or being equal as these for the substituent on Y.

Examples of imine ligands according to formula (2) include: guanidines, iminoimidazolines, phosphinimines, phenolimines, pyrroleimines, indoleimines and imidazoleimines.

R may be linked with Y, thus forming a ring system, optionally comprising hetero atoms, or optionally comprising functional groups. Examples of ligands comprising such ring systems include: 8-hydroxyquinoline, 8-aminoquinoline, 8-phosphinoquinoline, 8-thioquinoline, 8-hydroxyquinaldine, 8-aminoquinaldine, 8-phosphinoquinaldine, 8-thioquinaldine and 7-azaindole or indazole.

In the process of the invention, HA represents an acid, of which H represents its proton and A its conjugate base. Examples of A are halogenides, (such as fluoride, chloride, bromide, or iodide), sulfate, hydrogensulfate, phosphate, hydrogenphosphate, dihydrogenphosphate, carbonate, hydrogencarbonate, aromatic or aliphatic carboxylates, cyanide, tetrafluoroborate, (substituted) tetraphenylborates, fluorinated tetraarylborates, alkyl or aryl sulfonates.

In case the HA adduct of the imine ligand is used, one more equivalent of the base is required.

The metal is a metal chosen from group 3-11.

Examples of mono—or diacidic spectator ligand are ligands according to formula 5:

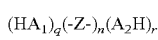 (formula 5), wherein $A_1$ and $A_2$ are monoacidic cyclopentadienyl comprising ligands (Cp), with q and r representing an integer denoting the number of Cp ligands with q+r=1 or 2, optionally linked by n bridging groups Z, with n representing the number of parallel bridges Z, $A_1$, $A_2$ when bonded via Z together forming a bidentate diacidic spectator ligand or if Z is absent $A_1$, $A_2$ form two monoacidic spectator ligands.

The ligands $A_1$ and $A_2$ are defined as cyclopentadienyl comprising ligands. Under cyclopentadienyl comprising ligands is understood that a part of the molecular structure contains a cyclopentadienyl (Cp) ring. This ring may be substituted with at least one R'-group. When the Cp-ring is substituted with at least two R' groups, these R' groups may form ring systems. As result of that the Cp-comprising ligand may be indenyl comprising ligands or fluorenyl comprising ligands. The ligands $A_1$ and $A_2$ may be each independently selected (substituted) cyclopentadienyl groups, (substituted) indenyl groups, (substituted)fluorenyl groups, (substituted) tetrahydroindenyl groups, (substituted) tetrahydrofluorenyl groups, (substituted) octahydrofluorenyl groups, (substituted) benzoindenyl groups, (substituted) heterocyclopentadienyl groups, (substituted) heteroindenyl groups, (substituted) heterofluorenyl groups, or its isomers. Here and in the following a hetero cyclopentadienyl group (in the following also referred to as 'hetero ligand') is understood to be a group that has been derived from a cyclopentadienyl group, but in which at least one of the C atoms in the 5-ring of the cyclopentadienyl has been replaced by a hetero atom, which hetero atom may be chosen from group 14, 15 or 16. If there is more than one hetero atom present in the 5-ring of the hetero ligand, these hetero atoms may be either the same or different. More preferably, the hetero atom has been chosen from group 15, while yet more preferably the hetero atom is phosphorus.

The R' groups may each independently be hydrogen or a hydrocarbon radical with 1-20 carbon atoms (e.g alkyl, aryl, biaryl, aralkyl, alkaryl and the like) or a heteroatom comprising moiety from group 13-17. Examples of such hydrocarbon radicals are methyl, ethyl, n-propyl, i-propyl, butyl (including isomers), hexyl (including isomers), decyl (including isomers), phenyl, biphenyl (including isomers) and the like. Examples of heteroatom comprising moieties of group 13-17 include borane radicals, silyl radicals, germyl radicals, stannyl radicals, amide radicals, phosphide radicals, oxide radicals, sulphide radicals, halide radicals, halide substituted hydrocarbyl radicals and the like. Also, two adjacent hydrocarbon radicals may be connected with each other in a ring system. Such a group as well may contain one or more R' groups as substituents. R' may also be a substituent which instead of or in addition to carbon and/or hydrogen may comprise one or more hetero atoms of groups 13-17.

The bridging group Z may contain $sp^3$, $sp^2$ or sp hybridized atoms of group 13 to 16 or combinations thereof. The bridging group Z may consist of linear, cyclic fragments, spiro ring systems, or combinations thereof. Examples of a carbon containing Z group may each separately be a hydrocarbon group with 1-20 carbon atoms, e.g. alkylidene, arylidene, biarylene, aryl alkylidene, etc. Examples of such groups are methylene, ethylene, propylene, butylene, phenylene, naphtylene, biphenylene, binaphtylene. Examples of silicium containing groups are dimethylsilyl, diethylsilyl, dipropylsilyl, including its isomers, (substituted) diphenylsilyl, dimethoxysilyl, diethoxysilyl, dipropoxysilyl, and diphenoxysilyl.

With a spectator ligand according to formula 2, a metalorganic compound according to formula 6 can be formed:

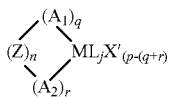

(formula 6)

wherein M is preferably a group 4-5 transition metal or a metal selected from the lanthanide series, and X' is an hydrocarbyl radical. X' may be independently chosen form the group of hydride, alkyl, siylyl, germyl, aryl, or a combination thereof. Preferably, X' is a hydride or a moiety selected form the group consisting of alkyl, aryl, silyl, germyl and combinations thereof (e.g. alkaryl, aralklyl, silyl, substituted alkyl, silyl substituted aryl, aryloxy alkyl, aryloxyaryl, alkoxyalkyl, amidoalkyl, amidoaryl, siloxyalkyl, siloxyaryl, amidosilyxyalkyl, haloalkyl, haloaryl, etc.) having up to 20 non-hydrogen atoms.

An example of a diacidic bidentate spectator ligand or a monoacidic bidentate spectator ligand is a ligand according to formula 7:

HCp*-Z—Y(H)$_b$ (formula 7)

in which Cp* is a delocalized $\eta^5$ bonding cyclopentadienyl comprising ligand, Z is a moiety comprising boron, or a member of Group 14, and optionally also sulfur or oxygen, said moiety having up to 20 non-hydrogen atoms, and optionally Cp* and Z together form a fused ring system, Y is a ligand bonded to Z comprising nitrogen, phosphorus, oxygen or sulfur and having up to 20 non-hydrogen atoms, optionally Y and Z together form a fused ring system and b=0 or 1. The mono-, or diacidic spectator ligand has 1 or 2 acidic protons, one of which is the acidic cyclopentadienyl proton. If the acidic spectator ligand contains only 1 proton (thus the cyclopentadienyl acidic proton), then b equals 0 and Y is a neutral two electron donor moiety. If the acidic spectator ligand contains 2 protons, then b equals 1 and Y contains an acidic proton.

The ligand Cp* represents a delocalized $\eta^5$ bonding cyclopentadienyl comprising ligand, which can be selected from the group of (substituted) cyclopentadienyl, (substituted) indenyl, (substituted) fluorenyl, such as (substituted) tetrahydroindenyl, (substituted) tetrahydrofluorenyl or (substituted) octahydroindenyl. Each carbon atom in the cyclopentadienyl comprising ligands may be substituted or unsubstituted. The substituents (on the cyclopentadienyl comprising ligands) may be the same or different. Examples of substituents include the following radicals: hydrocarbyl radicals, substituted-hydrocarbyl radicals wherein one or more hydrogen atoms is replaced by a halogen atom, hydrocarbyl-substituted metalloid radicals wherein the metalloid is selected from group 14, amido radicals, phosphido radicals, alkoxy radicals, sulphido radicals and halogen radicals. In addition two or more such substituents may together form a fused ring system. Suitable hydrocarbyl and substituted-hydrocarbyl radicals, which may be substituted for at least one hydrogen atom in the cyclopentadienyl radical, may contain from 1 to 20 carbon atoms and include straight and branched alkyl radicals, cyclic hydrocarbyl radicals, alkyl-substituted cyclic hydrocarbyl radicals, aromatic radicals and alkyl-substituted aromatic radicals, aralkyl radicals, silyl substituted alkyl radicals, silyl substituted aryl radicals, cyanoalkyl radicals, cyanoaryl radicals, haloalkyl radicals, haloaryl radicals, halosilyl radicals, etc. Suitable hydrocarbyl-substituted metalloid radicals include mono-, di- and trisubstituted organo-metalloid radicals of Group 14 elements wherein each of the hydrocarbyl groups contain from 1 to 20 carbon atoms. More particularly, suitable hydrocarbyl-substituted metalloid radicals include trimethylsilyl radicals, triethylsilyl radicals, ethyidimethylsilyl radicals, methyidiethylsilyl radicals, phenyldimethylsilyl radicals, methyidiphenylsilyl radicals, triphenylsilyl radicals, triphenylgermyl radicals, trimethylgermyl radicals and the like.

Y is —O—, —S—, —NR*—, —PR*—, or a neutral two electron donor ligand selected from the group consisting of OR*, SR*, NR*$_2$, or PR*$_2$.

Z is SiR*$_2$, CR*$_2$, SiR*$_2$SiR*$_2$, CR*$_2$CR*$_2$, CR*=CR*, CR*$_2$SiR*$_2$, GeR*$_2$, BR*, BR*$_2$; wherein each R* can be independently selected from the group consisting of hydrogen, alkyl, aryl, silyl, halogenated alkyl, halogenated aryl radicals, or combinations thereof (e.g. aralkyl, alkaryl, haloalkaryl and haloaralkyl radicals) having up to 20 non-hydrogen atoms, or two or more R* groups from Y, Z, or both Y and Z form a fused ring system.

With the spectator ligand of formula 7 a metal-organic compound is formed according to formula 8:

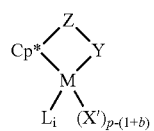

(formula 8)

wherein M is preferably a group 4-5 transition metal or a metal selected from the lanthanide series, and X' is an hydrocarbyl radical.

Another example of a monoacidic bidentate ligand (SH) is a) is a bi- or multidentate ligand, wherein S is represented by formula 9:

(Ar—Z—)$_s$Y(—Z-DR'$_n$)$_q$, (formula 9)

with,

Y represents an anionic moiety of S,

Z optional bridging groups between the Y moiety and the DR'$_n$ and/or Ar group, D an electron-donating hetero atom chosen form group 15 or 16, R' an optional substituent Ar an electron-donating aryl group, n the number of R' groups bonded to D, q and s integers with q+s≧1.

An example of a metal-organic compound formed with SH is a compound according to formula 10:

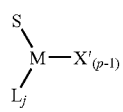

(formula 10)

wherein S is a multidentate monoanionic spectator ligand, comprising an electrodonating hetero atom containing group (DR'$_n$), or an electron donating aryl group, X' is an hydocarbyl radical bonded to M, L a neutral ligand bonded to M, j representing an integer denoting the number of ligands L.

The transition metal in a metal organic compound according to formula 10, is preferably chosen from groups 4-6 of the Periodic Table of the Elements. More preferably, the transition metal has been chosen from group 4, with the most preference to titanium (Ti) as transition metal. The transition metal in these metal-organic compounds, is preferably present in reduced form in the compound, which means that the transition metal is in a reduced oxidation state (p). By 'reduced oxidation state' is meant an oxidation state which is lower than the highest possible oxidation state for a particular metal, which means at most $M^{3+}$ for a transition metal of group 4, at most $M^{4+}$ for a transition metal of group 5 and at most $M^{5+}$ for a transition metal of group 6.

The bidentate monoanionic ligand is bonded covalently to the transition metal at one site, the anionic moiety (Y) and may be bonded coordinatively to the transition metal by a neutral Lewis basic site. A multidentate monoanionic ligand is a ligand, which is bonded covalently to the transition metal at one site and may be bonded coordinatively to the transition metal at several (tridentate, tetradentate, etc.) sites (via the D atom and/or Ar group(s)).

Examples of Y moieties include hydrocarbyl substituted groups comprising a group 15 or 16 atom, (substituted) cyclopentadienyl, (substituted) indenyl, (substituted) fluorenyl, (substituted) heterocyclopentadienyl, (substituted) heteroindenyl, (substituted) heterofluorenyl, or imine groups. Imine groups are defined as groups containing a double bonded nitrogen atom. Examples of imine groups are ketimide, guanidine, phosphinimide, iminoimidazoline, (hetero)aryloxyimines, pyrroleimines, indoleimines, imidazoleimines or (hetero)aryloxides, (substituted) pyridin-2-yl-methoxy, (substituted) quinolin-2-yl-methoxy, 8-hydroxyquinoline, 8-aminoquinoline, 8-phosphinoquinoline, 8-thioquinoline, 8-hydroxyquinaldine, 8-aminoquinaldine, 8-phosphinoquinaldine, 8-thioquinaldine and 7-azaindole or indazole, and the like.

The optional bridging group Z may contain $sp^3$, $sp^2$ or sp hybridized atoms or combinations thereof. The bridging group Z may consist of linear, cyclic fragments, or combinations thereof. The Z groups may each separately be a hydrocarbon group with 1-20 carbon atoms, e.g. alkylidene, arylidene, aryl alkylidene, etc. Examples of such groups are methylene, ethylene, propylene, butylene, biphenylene, binaphtylene, phenylene, whether or not with a substituted side chain, linear or cyclic.

Besides carbon, the main chain of the Z group may also contain larger members of group 14, such as silicon, germanium or tin. Examples of such Z groups are: dialkyl silylene, dialkyl germylene, tetra-alkyl disilylene or tetraalkyl silaethylene ($-SiR'_2CR'_2$).

The hetero atom containing donor group $DR'_n$ consists of at least one group 15 or group 16 atom, or a combination thereof. Examples of donor groups include imine groups as defined above, amine groups, phosphane groups, ether groups, or thioether groups.

Also, Y, Z and D may be part of an aromatic ring system, optionally containing $sp^3$, $sp^2$ or sp hybridized atoms or combinations thereof, together forming a spectator ligand. The D atom may thus be a part of the bridging group. In this case, the D atom containing bridging group may be further substituted by at least one optional bridging group Z containing donor groups $DR'_n$. Examples of spectator ligands containing aromatic ring systems having a donor atom D in the bridging group Z include (hetero)aryloxyimines, pyrroleimines, indoleimines, imidazoleimines or (hetero)aryloxides, (substituted) pyridin-2-yl-methoxy, (substituted) quinolin-2-yl-methoxy, 8-hydroxyquinoline, 8-aminoquinoline, 8-phosphinoquinoline, 8-thioquinoline, 8-hydroxyquinaldine, 8-aminoquinaldine, 8-phosphinoquinaldine, 8-thioquinaldine and 7-azaindole or indazole etc.

Preferably, the Y moiety may be an amido (—NR'—) group, a phosphido (—PR'—) group, an imine group, a (substituted) cyclopentadienyl group, a (substituted) indenyl group, a (substituted) fluorenyl group, a (substituted) heterocyclopentadienyl group, a (substituted) heteroindeny groupl, and a (substituted) heterofluorenyl group, Here and in the following a hetero cyclopentadienyl group (in the following also referred to as 'hetero ligand') is understood to be a group that has been derived from a cyclopentadienyl group, but in which at least one of the C atoms in the 5-ring of the cyclopentadienyl has been replaced by a hetero atom, which hetero atom may be chosen from group 14, 15 or 16 of the Periodic Table of the Elements. If there is more than one hetero atom present in the 5-ring of the hetero ligand, these hetero atoms may be either the same or different. More preferably, the hetero atom has been chosen from group 15, while yet more preferably the hetero atom is phosphorus.

Preferably, the electron donor group DR', consists of an electron-donating hetero atom D, chosen from group 15 or 16, and one or more substituents R' bonded to D. The number of R' groups is linked up with the nature of the hetero atom D, in the sense that n=2 if D is from group 15 and n=1 if D is from group 16. The substituent R' bonded to D is as defined. The hetero atom D has preferably been chosen from the group comprising nitrogen (N), oxygen (O), phosphorus (P) and sulphur (S); more preferably, the hetero atom is nitrogen (N) or phosphorus (P). It is further possible for two R' groups in the $DR'_n$ group to be connected with each other to form a ring-shaped structure (so that the DR' group can be a pyrrolidinyl group). The DR', group can form coordinative bonds with M.

The aromatic electron-donating group (or donor), Ar, used is a substituted or non-substituted aryl group ($C_6R'_5$), such as phenyl, tolyl, xylyl, mesitylyl, cumyl, tetramethyl phenyl, pentamethyl phenyl, etc. The Ar group may also contain at least one heteroatom from group 15 or group 16. Examples of such heteroatom containing (substituted) pyrrole, (substituted) pyridine, (substituted) thiophene, (substituted) furan. The coordination of this Ar or heteroatom containing Ar group in relation to M may vary from $\eta^1$ to $\eta^6$.

The R' groups may each separately be hydrogen or a hydrocarbon radical with 1-20 carbon atoms (e.g alkyl, aryl, aryl alkyl and the like). Examples of such hydrocarbon radicals are methyl, ethyl, propyl, butyl, hexyl, decyl, phenyl and the like. Also, two adjacent hydrocarbon radicals may be connected with each other in a ring system. As result from that, the Cp group may be an indenyl, tetrahydroindenyl, a fluorenyl, a tetrahydrofluorenyl, a octahydrofluorenyl or a benzoindenyl group. Such a group as well may contain one or more R' groups as substituents. R' may also be a substituent which instead of or in addition to carbon and/or hydrogen may comprise one or more hetero atoms of groups 14-16. Thus, a substituent may be a Si-containing group.

An example of a Lewis basic bi- or multidentate ligand is a ligand according to formula 11:

R-D-(Z-D)$_n$-R (formula 11)

wherein Z is a bridging group, between two donor atom containing groups (D), D an electron-donating group comprising a hetero atom chosen from group 15 or 16, and R is a substituent.

Examples of a Lewis basic bi-, or multidentate ligand are di-imines, tri-imines and di-imines comprising an aromatic hetero atom of group 15 or 16.

An example of a metal-organic compound formed with a spectator ligand according to formula 11 is a compound according to formula 12:

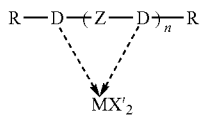

(formula 12)

With a ligand according to formula 11, in which each D may be the same or different, the metal preferably is a metal from Group 7-11, and X' is a hydrocarbyl radical.

The process of the invention is carried out in the presence of at least 2 equivalents of an organometal- or metalloid hydocarbyl compound. The amount of equivalents required for the process of the invention depends on the number of substitutable ligands X. A substitutable ligand is a ligand that can be substituted during the process and is thus not a spectator ligand.

The desired metal-organic compound is often formed instantaneously. Excess of the organometal- or metalloid hydocarbyl compound may be applied without negative effects on the reaction product. If the reaction is exothermic, the reaction mixture may be either cooled to a suitable temperature or the rate of addition of the base may be adjusted, or a combination thereof in order to control the reaction. If the reaction is slow, the reaction mixture may be heated in order to increase the reaction rate. During the reaction, a salt is formed. The reaction mixture as obtained by contacting a spectator ligand with the metal-organic reagent may be used as precatalyst in a polyolefin polymerisation without an additional filtration step if the salt formed during the reaction is compatible with the polymerisation process. If a salt free metal-organic compound is required, the salt can be removed by using a filtration. Depending on the solubility of the metal-organic compound, the mixture may be heated and then filtered. An advantage of the present invention is that the filtrate may be used as such without further purification in a following polimerisationprocess. If desired, the metal-organic compound may be isolated by distillation of the solvent, by precipitation or by crystallisation from a suitable solvent.

The process of the invention is preferably carried out in a solvent. Suitable solvents are solvents that do not react with the metal organic reagent or the metal organic compound formed in the process of the invention. Examples of suitable solvents include aromatic and aliphatic hydrocarbons, halogenated hydrocarbons, amides of the aliphatic carboxylic acids and primary or secondary, amines, DMSO, nitromethane, benzonitrile, ethers, polyethers, cyclic ethers, lower aromatic and aliphatic ethers, pyridine, alkylpyridines, cyclic and linear primary, secondary, tertiary amines, or mixtures thereof. Preferred solvents include aromatic or aliphatic hydrocarbons or mixtures thereof.

With the method of the invention two new classes of compounds can be prepared.

The invention therefore further relates to a hydrocarbylated metal organic compound according to formula 10, containing a spectator ligand according to formula 9, characterized in that Y is an imine radical. Preferably the imine is a ketimide, phosphinimide, guanidine, or iminoimidazoline. Other preferred imines are spectator ligands wherein Y, R and D are part of an aromatic ring system, optionally containing $sp^3$, $sp^2$ or sp hybridized atoms or combinations thereof. Examples of these imines include: (hetero)aryloxyimine (like (substituted) derivatives of phenoxyimines, pyrroleimines, hydroyquinolines and the like) (hetero)arylsulphidoimine, (hetero)arylphosphidoimine and (hetero)arylamidoimine.

Further preferences of the metal organic compounds according to the invention are those hydrocarbylated metal organic compounds wherein Y is an imine and wherein the donor D is a ketimine, phosphinimine, guanidine, or iminoimidazoline.

The invention also relates to a hydrocarbylated metal organic compound according to formula 10, containing a spectator ligand according to formula 9, characterized in that D is a ketimide, phosphinimide, guanidine, or an iminoimidazoline.

These new hydrocarbylated metal organic compounds turned out to be excellent catalysts in the polymerisation of polyolefines.

The invention further relates to a process for the preparation of a polyolefin in the presence of an activator, characterized in that the process is carried out in the presence of a metal-organic compound formed, by contacting a spectator ligand, with a metal-organic reagent in the presence of at least 2 equivalents of a hydrocarbylating agent. An advantage of the metal-organic compounds formed according to the invention is, that they are highly active when used in combination with boranes or borates. Well known boranes and borates used as activator in the preparation of polyolefins are described in Chem. Rev., 2000, 100, 1391 by E. Y-X. Chen and T. J. Marks.

The invention will be elucidated with some non-limiting examples.

General Part

Experiments were performed under a dry and oxygen-free nitrogen atmosphere using Schlenk-line techniques. $^1$H-NMR, $^{13}$C-NMR-spectra and $^{31}$P-NMR-spectra were measured on a Bruker Avance 300 spectrometer. Ligroin was distilled from sodium/potassium alloy; THF and toluene from potassium and sodium, respectively, all having benzophenone as indicator. Other starting materials were used as obtained.

EXAMPLE I

One-Step Preparation of $(Cp-C_6F_5)Ti(NP(t-Bu)_3)$ $Me_2$ from Tri-tert-butyl Aminophosphonium Chloride $(tBu_3PClNH_2)$ and $Cp(C_6F_5)TiCl_3$ using methylmagnesiumbromide To an orange mixture of $C_6F_5CpTiCl_3$ (1.00 g, 2.59 mmol) and t-$Bu_3PClNH_2$ (0.68 g, 2.59 mmol) in toluene (60 mL) and THF (20 mL) was added a MeMgBr solution in ether (3.0M, 4.0 mL, 12 mmol) at −20° C. The reaction mixture was stirred for 45 minutes and subsequently dried in vacuo. The residue was extracted with boiling ligroin (20 and 40 mL respectively). The solvents were removed in vacuo resulting in 1.33 g (98%) of $(Cp-C_6F_5)Ti(NP(t-Bu)_3)Me_2$ with no detectable amounts of by-product.

EXAMPLE II

Synthesis of 1,3-bis(2,6-dimethylphenyl)-iminoimidazoline cyclopentadienyl titanium dimethyl using methylmagnesium bromide To a suspension of 1,3-bis(2,6-dimethylphenyl)-iminoimidazoline (2.93 g, 10.0 mmol) and cyclopentadienyltitanium trichloride (2.19 g, 10.0 mmol) in toluene (100 mL) was added methylmagnesiumbromide (11 mL of a 3.0 M solution in diethyl ether, 33 mmol) at −80° C. during 10 minutes. The mixture was allowed to warm to ambient temperature to give a yellow suspension. THF (30 mL) was added, and the mixture was stirred for 15 hours. The light yellow suspension was evaporated to dryness. The residue was extracted with boiling ligroin (100 mL). The resulting suspension was filtered hot. The cake was extracted further with hot ligroin (Three times with 60 mL until the filtrate became colourless). The combined yellow filtrates were partially evaporated under reduced pressure to 50 mL. Cooling to approximately 4° C. afforded yellow crystals, which were filtered and washed with cold ligroin to give 2.05 g (47% yield) of NMR pure 1,3-bis (2,6-dimethylphenyl)-iminoimidazoline cyclopentadienyl titanium dimethyl.

EXAMPLE III

Synthesis of tris(N,N-dimethylamido)phosphoraneimido cyclopentadienyl titanium(IV) dimethyl To a solution of cyclopentadienyltitanium trichloride (0.51 g, 2.3 mmol) and N,N,N',N',N",N"-hexamethylphosphorimidic triamide (0.44 g, 2.5 mmol) in toluene (40 mL) and THF (10 mL) was added a solution of methylmagnesium bromide in ether (2.3 mL, 3.0 M, 6.9 mmol) at room temperature. The reaction was exothermal under gas evolution and the colour changed to light yellow. $^{31}$P-NMR reaction monitoring showed that the desired product was formed without any detectable amount of by-product. The solvents were removed in vacuo and the product was extracted from the residue with n-hexane twice (50 mL each). The solvents were removed in vacuo to give 0.59 g (yield: 79%) of a yellow powder, which was characterized by $^1$H- and $^{31}$P-NMR to be tris(N,N-dimethylamido)phosphoraneimido cyclopentadienyl titanium (IV) dimethyl.

The invention claimed is:

1. Process for the preparation of a hydrocarbylated metal organic compound, comprising a hydrocarbyl group, a spectator ligand and optionally a ligand, by contacting a metal-organic reagent with a spectator ligand in the presence of at least 2 equivalents, with respect to the metal-organic reagent, of a hydrocarbylating agent.

2. Process according to claim 1, wherein the hydrocarbylating agent comprises a metal or a metalloid chosen from group consisting of 1, 2, 11, 12, 13 and 14.

3. Process according to claim 2, wherein the hydrocarbylating agent comprises Li, Mg, Zn, or Al.

4. A process according to claim 1, wherein the spectator ligand is an imine ligand, or an HA adduct of an imine ligand, wherein HA represents an acid, of which H represents its proton and A its conjugate base.

5. A process according to claim 4, wherein the metal of the metal-organic reagent is a group 3-11 metal.

6. A process according to claim 1, wherein the spectator ligand is represented by $(HA_1)_q(-Z-)_n(A_2H)_r$, wherein $A_1$ and $A_2$ are monoacidic cyclopentadienyl comprising ligands, with q and r representing an integer denoting the number of Cp ligands with q+r=1 or 2, optionally linked by n bridging groups Z, $A_1$, $A_2$ separately, or bonded via Z together forming a bidentate diacidic spectator ligand and n being an integer denoting the number of parallel bridging groups Z.

7. A process according to claim 1,
wherein the ligand is a ligand according to the formula HCp*-Z—Y(H)$_b$,
in which Cp* is a delocalized $\eta^5$ bonding cyclopentadienyl comprising ligand,
wherein Y is a ligand bonded to Z comprising nitrogen, phosphorus, oxygen or sulfur and having up to 20 non-hydrogen atoms,
wherein Z is a moiety comprising boron, or a member of Group 14, and also sulfur or oxygen, said moiety having up to 20 non-hydrogen atoms, and
optionally Cp* and Z together form a fused ring system and b=0 or 1.

8. A process according to claim 6, wherein the metal is a group 4, or 5 metal or metalloid, or a metal selected from the lanthanide series.

9. A process according to claim 1, wherein the ligand, represented by $(Ar—Z—)_sY(—Z-DR'_n)_q$, with, Y representing an anionic moiety, Z an optional bridging group between the Y moiety and the DR'$_n$ and/or Ar group, D an electron-donating hetero atom chosen from group 15 or 16, R' an optional substituent, Ar an electron-donating aryl group, n the number of R' groups bonded to D, q and s integers with q+s≧1.

10. A process according to claim 9, wherein the metal is a group 4 metal with a valency of 3.

11. A process according to claim 1, wherein the ligand is represented by

R-D-(Z-D)$_n$R wherein Z is a bridging group, between two donor atom containing groups (D), D an electron-donating group comprising a hetero atom chosen from group 15 or 16, n is the number of (Z-D) groups, and R is a substituent.

12. A process according to claim 11, wherein the metal is a metal from group 7-11.

* * * * *